United States Patent [19]

Sakamoto et al.

[11] Patent Number: 5,270,046
[45] Date of Patent: Dec. 14, 1993

[54] HEPARIN BOUND ANTI-THROMBOTIC MATERIAL

[75] Inventors: Nagayoshi Sakamoto; Kazutoshi Iida, both of Ichihara, Japan

[73] Assignee: Ube Industries, Ltd., Ube, Japan

[21] Appl. No.: 787,776

[22] Filed: Nov. 6, 1991

Related U.S. Application Data

[63] Continuation of Ser. No. 464,658, Jan. 11, 1990, abandoned, which is a continuation of Ser. No. 249,832, Sep. 27, 1988, abandoned.

[51] Int. Cl.$^5$ .............................................. A61F 2/00
[52] U.S. Cl. .................................. 424/422; 424/423; 523/112; 526/238.2; 526/238.21; 526/238.22; 526/238.23; 526/238.3; 514/822; 536/21
[58] Field of Search ............. 523/112; 526/238.2, 526/238.21, 238.22, 238.23, 238.3; 514/822; 536/21; 424/78.08, 78.18, 78.31, 422, 423

[56] References Cited

U.S. PATENT DOCUMENTS

| | | | |
|---|---|---|---|
| 3,673,612 | 7/1972 | Merrill | 526/238.2 |
| 3,766,104 | 10/1973 | Bonin | 523/112 |
| 3,844,989 | 10/1974 | Harumiya | 514/827 |
| 3,846,353 | 11/1974 | Grotta | 523/112 |
| 3,853,804 | 12/1974 | Yew | 523/112 |
| 5,069,899 | 12/1991 | Whitbourne | 523/112 |

FOREIGN PATENT DOCUMENTS

| | | |
|---|---|---|
| 91117 | 11/1971 | Japan . |
| 36779 | 9/1977 | Japan . |
| 17797 | 7/1979 | Japan . |
| 18317 | 7/1979 | Japan . |
| 18518 | 7/1979 | Japan . |
| 38963 | 10/1980 | Japan . |
| 38964 | 10/1980 | Japan . |
| 56-104670 | 8/1981 | Japan . |
| 34494 | 7/1983 | Japan . |
| 0114013 | 7/1983 | Japan . |
| 50335 | 12/1984 | Japan . |
| 53058 | 12/1984 | Japan . |
| 16260 | 4/1985 | Japan . |
| 23626 | 6/1985 | Japan . |
| 61-20309 | 5/1986 | Japan . |
| 61-168355 | 7/1986 | Japan . |
| 105767 | 5/1988 | Japan . |
| 1-080368 | 3/1989 | Japan . |

Primary Examiner—Thurman K. Page
Assistant Examiner—G. S. Kishore
Attorney, Agent, or Firm—Frishauf, Holtz, Goodman & Woodward

[57] ABSTRACT

Disclosed is an anticoagulant material comprising a polymer obtained from an ionically bonded composite synthesized from i) a basic compound having a copolymerizable functional group and ii) a heparin salt. Disclosed is also a process for preparing the anticoagulant material. The anticoagulant material of the present invention can maintain excellent anticoagulant properties or antithrombotic properties over a long period of time and is capable of being applied as a component material for various medical articles such as artificial internal organs and artificial blood vessels, and a process for preparing it.

12 Claims, No Drawings

HEPARIN BOUND ANTI-THROMBOTIC MATERIAL

This application is a continuation of application Ser. No. 07/464,658, filed Jan. 11, 1990 (abandoned), which is a continuation of application Ser. No. 07/249,832 filed on Sep. 27, 1988 (abandoned).

BACKGROUND OF THE INVENTION

This invention relates to an anticoagulant material that can maintain excellent anticoagulant properties (or antithrombotic properties) over a long period of time and is capable of being applied as a component material for various medical articles such as artificial internal organs and artificial blood vessels, and a process for preparing it.

Blood has a property of being coagulated by the action of various components in blood when it has come into contact with foreign matters. Hence, a high anticoagulant property is required in component materials for medical articles or instruments used on the part coming into contact with blood, as exemplified by artificial hearts, artificial cardiac valves, artificial blood vessel, blood vessel catheters, cannulas, pump-oxygenators, blood vessel by-pass tubes, intraaortic balloon pumping, transfusion instruments and extracorporeal circulation circuits. However, many of conventional component materials for the medical articles or instruments may unavoidably cause blood coagulation when used over a long period of time, and thus can not be satisfactory in view of the power to maintain anticoagulant properties. Also, when the above medical articles are applied to patients, it has been commonly practiced to use together an anticoagulant such as heparin. However, when, for example, the heparin is systemically administered, there is the problem that a large number of bleeding nests are tend to be generated with high possibility.

Accordingly, as means for eliminating such problems, a number of methods have been attempted to introduce heparin into anticoagulant materials. The methods of introducing heparin into such materials can be roughly grouped into three methods.

They include firstly a method in which heparin is physically mixed to introduce it into the materials; secondly a method in which heparin and a constituent of the materials are brought into covalent bonding; and thirdly a method in which an anionic residual group of heparin and a cationic residual group of a constituent of the materials are brought into ionic bonding. Also available is a method in which any of these methods are combined.

Such methods, however, have various problems. In the first method, the heparin, though soluble in water, is insoluble in almost all of organic solvents, and hence there is brought about a great limitation in its specific manner or in the materials that can be used. Also, since the heparin introduced into the materials is water-soluble, it flows out of the materials in a very short time when it comes into contact with blood in its practical use, so that the anticoagulant properties can not be maintained.

The second method has the problems such that because of the covalent bonding effected by utilizing a reactive residual group of heparin, the materials can be synthesized with complicacy and also the anticoagulant properties of the heparin itself may be lowered.

As an example of the third method, disclosed in Science, Vol. 142, p.1297 (1963) is a method in which the surface of a material is treated with graphite-benzalkonium chloride-heparin, and also disclosed in Japanese Unexamined Patent Publication No. 55946/1973 is a polymeric material obtained by confining a heparin-cationic surface active agent, a radically polymerizable vinyl monomer and a polymerization initiator into a stereocomplex composed of an isotactic polymethyl methacrylate and a syndiotactic polymethyl methacrylate, followed by polymerization of said monomer. Since, however, in any case the heparin is formed into a composite with a low molecular ammonium salt such as benzalkonium chloride by ionic bonding, heparin may still flow into blood in a short period of time, and not only the heparin but also the low molecular ammonium salt may simultaneously flow out, thus bringing about a serious problem that a hemolysis is caused.

Also proposed is a method in which a polymeric compound into which a cationic residual group has been introduced is brought into contact with an aqueous heparin solution, thereby introducing heparin into the polymeric compound through ionic bonding. For example, disclosed in Japanese Patent Publications No. 36779/1977, No. 17797/1979, No. 18317/1979, No. 38963/1980 and No. 38964/1980 is a method in which a cationic residual group is introduced into a copolymer such as a vinyl chloride/acrylonitrile copolymer by graft polymerization, and thereafter heparin is introduced, and disclosed in Japanese Patent Publications No. 34494/1983, No. 50335/1984, No. 53058/1984, No. 16260/1985, No. 23626/1985 and No. 20309/1986 is a method i" which a cationic residual group is introduced by copolymerization, addition polymerization or condensation polymerization, and then heparin is introduced, or a method in which a heparin-introduced composite is blended with a polymeric component having a good strength. In any of such methods, however, the amount of heparin introduced in the polymeric compound may greatly vary depending on the amount of the cationic residual group present in the above compound or the chemical and physical properties of the polymeric compound, such as water absorption properties based on the degree of hydrophilic nature of the above compound, as well as the temperature, time or the like used when the polymeric compound is brought into contact with heparin. Accordingly, it is difficult to set optimum conditions also when a desired amount of heparin is intended to be introduced, so that the quality of the resulting anticoagulant materials can not be made constant.

Also, in the materials obtained by the above-mentioned methods, the polycationic polymeric material and the polyanionic heparin are supported by the interpolymer reaction, and hence it may not occur that the cationic residual group and the anionic residual group are bonded in a stoichiometrically 1:1 fashion, resulting in nothing more than ion formation on part of the polymer. Consequently, heparin may flow out when it comes into contact with blood. In other words, what are realized in such methods are anticoagulant materials that are gradually heparin-releasing. Thus, heparin may finally disappear after they are placed in blood for a long time. Taking account of the flowing-out of heparin like this, Japanese Patent Publication No. 18518/1979 teaches that in the heparin-introduced material, the anionic residual group originating from heparin is required to be present in excess on the surface thereof so that a standard film potential difference may indicate a negative value.

Namely, the material obtained by such a method is a material that has been made gradually heparin-releasing like the material obtained by the above first method. Although the degree by which the heparin is released is suppressed as compared with that of the material obtained by the above first method and an improvement is seen in the anticoagulant properties, the material is still not satisfactory as to long-term antithrombotic properties, thus leaving room for further improvement.

Heparin-introduced anticoagulant materials having been hitherto applied as component materials of medical articles such as artificial internal organs and artificial blood vessels have the problem that the heparin having been introduced into the materials gradually flows into blood and comes to disappear during their use, resulting in a lowering of the anticoagulant properties of the materials with lapse of time. They have also additional problems that the manner of introducing heparin is complicated and no anticoagulant material having constant quality can be obtained.

SUMMARY OF THE INVENTION

An object of this invention s to provide an anticoagulant material and a process for preparing the same, that can eliminate the problems stated above, can introduce heparin into a polymeric material in the form of a composite by a simple method, and, in an anticoagulant material having the above composite as a component factor, in which heparin is firmly held inside or on the of the material, can maintain superior anticoagulant properties over a long period of time.

The present inventors have noted that in an anticoagulant material into which a heparin salt has been introduced, an attempt to restrain the water-soluble heparin salt from flowing into blood to maintain anticoagulant properties can be achieved by bringing the introduced heparin salt to be held in a slightly water-soluble form and further bringing the heparin salt to be held by the action based on a physical structure of the anticoagulant material itself. This invention has been thus accomplished.

Namely, this invention relates to an anticoagulant material comprising a polymer obtained from an ionically bonded composite synthesized from i) a basic compound having a copolymerizable functional group and ii) a heparin salt.

As a preferred embodiment, the ionic bonding in said ionically bonded composite is effected in substantially ion equivalent weight in said polymer and the heparin salt is not substantially gradually released at a physiologic temperature.

As another preferred embodiment, the anticoagulant material of this invention comprises a polymer obtained from the ionically bonded composite and at least one of a hydrophilic monomer and a hydrophobic monomer that are copolymerizable with the ionically bonded composite and, optionally, a cross-linking agent.

As a further preferred embodiment, the anticoagulant material comprises the polymer and a polymeric compound serving as a matrix.

Hereinafter, on account of readiness to explain, the ionically bonded composite is called as to component (a); at least one of a hydrophilic monomer and a hydrophobic monomer, component (b); the cross-linking agent, component (c); the polymer obtained from (a), (b) and, optionally (c), component (A); and the polymeric compound serving as a matrix, component (B).

The polymer of Component (A) constituting the anticoagulant material of this invention is prepared from Components (a) and (b) and Component (c) that is optionally used.

DESCRIPTION OF THE PREFERRED EMBODIMENTS

The Component (a) ionically bonded composite is prepared from i) a basic compound having a copolymerizable functional group and ii) a heparin salt, and is slightly soluble in water and also soluble in an organic solvent.

The basic compound used here, having a copolymerizable functional group, is a compound having, for example, a vinyl group, an acryloyl group, a methacryloyl group or the like as the copolymerizable functional group, also having, for example, a tertiary amino group, a quaternary ammonium group or a quaternary pyridinium group as a basic residual group, and capable of undergoing ionic bonding to the heparin salt to form a composite that is slightly soluble in water and soluble in an organic solvent. Such a basic compound may include, for example, a compound represented by the following Formula (I):

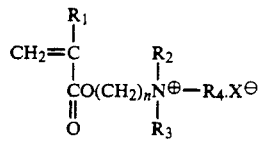

wherein $R_1$ represents a hydrogen, atom or a methyl group; $R_2$ and $R_3$ may be the same or different and each represent an alkyl group having 1 to 3 carbon atoms; $R_4$ represents an alkyl group having 6 to 22 carbon atoms; X represents a group of negative atoms; and n represents an integer of 1 to 6;

or a compound represented by the following Formula (II):

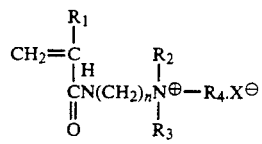

wherein each symbol has the same meaning as in Formula (I).

In the compound represented by Formula (I) or (II), the group $R_4$ may preferably be an alkyl group having 8 to 18 carbon atoms in order to make the ionically bonded composite slightly soluble in water and also soluble in an organic solvent, and on account of readiness to handle.

The group of negative atoms represented by X may preferably include halogen atoms.

Example of the compound represented by the above Formula (I) may include;

N,N-dimethyl-N-hexylammonioethyl acrylate or methacrylate bromide,

N,N-dimethyl-N-octylammonioethyl acrylate or methacrylate bromide,

N,N-dimethyl-N-decylammonioethyl acrylate or methacrylate bromide,

N,N-dimethyl-N-dodecylammonioethyl acrylate or methacrylate bromide,
N,N-dimethyl-N-tetradecylammonioethyl acrylate or methacrylate bromide,
N,N-dimethyl-N-hexadecylammonioethyl acrylate or methacrylate bromide,
N,N-dimethyl-N-octadecylammonioethyl acrylate or methacrylate bromide,
N,N-dimethyl-N-eicosylamnonioethyl acrylate or methacrylate bromide, and
N,N-dimethyl-N-docosylammonioethyl acrylate or methacrylate bromide.

Example of the compound represented by the above Formula (II) may also include;
N(N',N'-dimethyl-N'-hexylammoniopropyl) acrylate or methacrylate bromide,
N(N',N'-dimethyl-N'-octylammoniopropyl) acrylate or methacrylate bromide,
N(N',N'-dimethyl-N'-decylammoniopropyl) acrylate or methacrylate bromide,
N(N',N'-dimethyl-N'-dodecylammoniopropyl) acrylate or methacrylate bromide,
N(N',N'-dimethyl-N'-tetradecylammoniopropyl) acrylate or methacrylate bromide,
N(N',N'-dimethyl-N'-hexadecylammoniopropyl) acrylate or methacrylate bromide,
N(N',N'-dimethyl-N'-octadecylammoniopropyl) acrylate or methacrylate bromide,
N(N',N'-dimethyl-N'-eicosylammoniopropyl) acrylate or methacrylate bromide, and
N(N',N'-dimethyl-N'-docosylammoniopropyl) acrylate or methacrylate bromide.

Such compound represented by Formula (I) or (II) can be synthesized according to the following reaction scheme (1) or (2).

Reaction scheme (1):

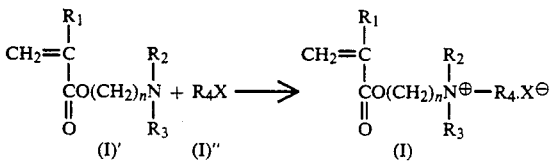

Reaction scheme (2):

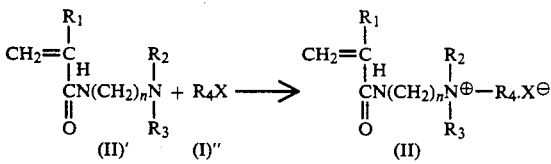

A method of synthesizing the basic compound will be described below in detail on the bases of the above reaction schemes (1) and (2). First, the compound represented by Formula (I)' or (II)' and the compound represented by Formula (I)'' an equimolar amount are added in an organic solvent such as dimethylformamide to effect dissolution. Subsequently, after a polymerization inhibitor such as dibutylhydroxytoluene is added, reaction with heating may be carried out at temperatures of from 60° to 80° C. for several hours to several ten hours, thereby obtaining the compound represented by Formula (I) or (II).

Examples of the compound represented by Formula (I)', used in reaction scheme (I) may include N,N-dimethylaminomethyl acrylate or methacrylate,
N,N-dimethylaminoethyl acrylate or methacrylate,
N,N-dimethylaminopropyl acrylate or methacrylate,
N,N-dimethylaminobutyl acrylate or methacrylate,
N,N-dimethylaminohexyl acrylate or methacrylate,
N,N-diethylaminoethyl acrylate or methacrylate,
N,N-dipropylaminoethyl acrylate or methacrylate.

Examples of the compound represented by Formula (I)'' may include hexyl bromide, octyl bromide, decyl bromide, dodecyl bromide, tetradecyl bromide, hexadecyl bromide, octadecyl bromide, eicosyl bromide and docosyl bromide, or chlorides or iodides respectively corresponding to these.

Examples of the compound represented by Formula (II)', used in reaction scheme (2) may include
N(N',N'-dimethylaminoethyl) acrylate or methacrylate,
N(N',N'-dimethylaminopropyl) acrylate or methacrylate,
N(N',N'-dimethylaminobutyl) acrylate or methacrylate,
N(N',N'-dimethylaminohexyl) acrylate or methacrylate,
N(N',N'-diethylaminopropyl) acrylate or methacrylate, and
N(N',N'-dipropylaminopropyl) acrylate or methacrylate.

The ionically bonded composite can be prepared by reacting an aqueous solution of monomers of the above basic compound having a copolymerizable functional group with an aqueous solution of the heparin salt.

In the heparin salt used here, there is no particular limitation in the type of the salt, but commonly used is sodium heparin.

Amounts of the basic compound and the heparin salt which are used in the reaction may preferably be such that when, for example, the compound represented by Formula (I) or (II) and sodium heparin are used, the compound represented by Formula (I) or (II) is used in an amount of from 1 to 12 mmol, more preferably of from 2 to 8 mmol, based on 1 g of sodium heparin.

The reaction may be carried out at a temperature of from 10° to 40° C., preferably from 15° to 30° C., for a period of from 10 to 300 minutes, preferably from 30 to 180 minutes.

The ionically bonded composite can be obtained in this manner. Because of a relatively low molecular weight of the compound having a cationic group as compared with the conventional heparin-introducing means utilizing the contact between a polymeric material having a cationic group and an aqueous solution of a heparin salt, the above method brings the above compound and heparin salt to be bonded at a larger number of bonding points, so that the heparin salt can be more firmly held after polymerization. More specifically, in the ionically bonded composite in this invention, the basic compound having a copolymerizable functional group undergoes ionic bonding to an anionic residual group of heparin in substantially ion equivalent weight. This can be evidenced by the fact that the amount of sodium in the ionically bonded composite produced when sodium heparin is used as the heparin salt is usually 1% or less and substantially 0% as an ash content value in elementary analysis. Accordingly, although the amount of the heparin salt in the ionically bonded composite depends on the molecular weight of the basic compound having a copolymerizable functional group or the amount of the anionic residual group of the heparin salt, the heparin salt may preferably be contained so as to be 0.5 to 12% by weight as the amount of the sulfur contained in the heparin salt, in order to retain anticoagulant properties at a given level. Similarly, the heparin salt may more preferably be contained so as to be 1 to 8% by weight.

Such Compound (a) ionically bonded composite may be mixed in an amount of from 5 to 99.5% by weight, preferably from 10 to 90% by weight, based on the total amount of Components (a) to (c). The mixing amount for Component (a) that is otherwise less than 5% by weight may result in insufficiency in anticoagulant properties of the anticoagulant material, and the amount otherwise more than 99.5% by weight may result in insufficiency in mechanical strength of the above anticoagulant material.

Usable as the Component (b) hydrophilic monomer that is copolymerizable with the Component (a) ionically bonded composite is at least one selected from the group consisting of, for example, sodium acrylate or methacrylate, acryl- or methacrylamide, N-methyl acrylamide, acrylglycine amide, hydroxyethyl acrylate or methacrylate, methoxypolyethylene glycol acrylate or methacrylate, N-vinyl-pyrrolidone, N-vinyl-lactam, and diacetone acrylamide. Similarly, usable as the hydrophobic monomer is at least one selected from the group consisting of, for example, styrene, vinyl chloride, vinyl acetate, methyl acrylate or methacrylate, acrylo- or methacrylonitrile, alkyl-substituted styrenes, vinyl isobutyl ether, vinyl propionate, and vinyl butyrate.

Such hydrophilic monomer and hydrophobic monomer can be selected whether they are respectively used alone or in combination, depending on what the resulting anticoagulant material is used for, in other words, depending on the degree of the hydrophilic nature required in the material.

Such Component (b) may be mixed in an amount of from 0.05 to 95% by weight, preferably from 0.1 to 90% by weight, based on the total amount of Components (a) to (c). The mixing proportion of the above monomer otherwise less than 0.05% by weight may result in insufficiency in anticoagulant properties of the anticoagulant material, and the proportion otherwise more than 95% by weight may result in insufficiency in mechanical strength of the material.

The mixing of the Component (c) cross-linking agent is supposed to give a Component (A) polymer having such structure that the anticoagulant material can be brought to have an interpenetrating or entangling construction comprised of the Component (A) polymer and the Component (B) matrix. Bringing the anticoagulant material to have such an interpenetrating or entangling construction can not only further increase the power to hold the heparin salt, but also enhance mechanical properties such as elasticity of the material, thus making the material more desirable as component materials for medical articles.

Usable as the Component (c) cross-linking agent is at least one, selected from the group consisting of, for example, divinylbenzene, alkylenebisacryl- or mathacrylamides such as methylenebisacryl- or methacrylamide and ethylenebisacryl- or methacrylamide, alkylene glycol diacrylates or dimethacrylates such as ethylene glycol diacrylate or dimethacrylate and propylene glycol diacrylate or dimethacrylate, and diethylene glycol diacrylate or dimethacrylate.

Such Component (c) may be mixed in the proportion of from 0 to 60% by weight, preferably from 0.05 to 40% by weight, based on the total amount of Components (a) to (c). The mixing proportion of Component (c) otherwise more than 60% by weight may result in insufficiency in mechanical strength of the anticoagulant material.

As described later, the above Components (a) to (c) exist in the anticoagulant material in the form of a polymer obtained from these.

The polymeric compound (B) that constitutes the anticoagulant material of this invention together with the Component (A) polymer exists in the material in the form of a matrix. Such a polymeric compound (B) is required to be soluble in an organic solvent or capable of swelling in it, and there can be used, for example, polyvinyl chloride, polyvinyl acetate, polyacrylonitrile, polyepichlorohydrin, polyester, polyurethane, polyurethaneurea, acetyl cellulose, and polyhydroxyethyl acrylate or methacrylate, or copolymers of two or more kinds selected from these or mixtures of any of these. Such polymeric compounds can be appropriately selected depending on the types of the medical articles to which the resulting anticoagulant materials are applied, but, in usual cases, preferred from the viewpoints of rich flexibility and excellent mechanical strength is polyurethane or polyurethaneurea.

The anticoagulant material of this invention can be obtained by using the above Components (a) to (c) and Component (B) in respectively prescribed amounts, blending them to a uniform state, and thereafter effecting polymerization.

In this occasion, Components (a) to (c) and Component (B) may be mixed in the manner that the amount of Component (B) ranges from 10 to 1,900 parts by weight, preferably from 20 to 900 parts by weight, based on 100 parts by weight of the total amount of Components (a) to (c). The mixing amount of Component (B) otherwise less than 10 parts by weight may result in insufficiency in mechanical strength of the anticoagulant material, and the amount more than 1,900 parts by weight may result in insufficiency in anticoagulant properties of the material.

In mixing Components (a) to (c) and Component (B), an organic solvent may be optionally used. Such an organic solvent may include at least one selected from the group consisting of, for example, dimethylformamide, dimethylacetamide, dimethylsulfoxide, tetrahydrofuran, ethyl alcohol, propyl alcohol, butyl alcohol, dioxane, and N-methylpyrrolidone.

There is no particular limitation in mixing methods, and any methods may be used so long as the respective components can be mixed in a uniform state.

Applicable as a polymerization method is radical polymerization or ionic polymerization, but preferred among these is radical polymerization. In carrying out radical polymerization, a polymerization initiator may be optionally used. This polymerization initiator may include, for example, azo compounds such as azobisisobutyronitrile; and organic peroxides including hydroperoxides such as t-butyl hydroperoxide and cumene hydroperoxide, dialkyl peroxides such as di-t-butyl peroxide and dicumyl peroxide, and diacyl peroxides such as lauroyl peroxide and benzoyl peroxide. Such polymerization initiators may be added in an amount of approximately from $5 \times 10^{-4}$ to 10% by weight based on the total amount of Components (a) to (c) and Component (B).

The polymerization may be carried out at a temperature of from normal temperature to 100° C., preferably from 40° to 90° C. It may also be carried out for a period of from 1 hour to 5 days, preferably from 2 hours to 3 days.

Thus the anticoagulant material of this invention can be obtained. In the anticoagulant material of this invention thus obtained, the amount of sodium in the ionically bonded composite used is substantially 0% as an ash content value in elementary analysis, and hence the amount of sodium in the anticoagulant material to be finally obtained in this invention is substantially 0% as an ash content value in elementary analysis. Also, in the anticoagulant material of this invention, the Component (A) polymer and Component (B) polymeric compound exist in a physically bonded state (where the interpenetrating or entangling construction is formed by cross-linking attributable to ionic bonding of the heparin which is a polyanionic polymer in the case when the Component (c) cross-linking agent is not used, and by covalent bonding in addition to the above cross-linking attributable to ionic bonding in the case when the Component (c) cross-linking agent is used as an essential component.) However, the anticoagulant material of this invention includes not only the materials available in such a physically bonded state but also those available in the state that Component (A) and Component (B) are chemically bonded in part. Such anticoagulant materials are useful as component materials for medical articles or instruments used on the part coming into contact with blood, as exemplified by artificial hearts, artificial cardiac valves, artificial blood vessel, blood vessel catheters, cannulas, pump-oxygenators, blood vessel by-pass tubes, intraaortic balloon pumping, transfusion instruments and extracorporeal circulation circuits.

EXAMPLES

This invention will be described below in greater detail. In the following, "%" indicates "% by weight" in all instances.

Example 1

Dissolved in 80 ml of dimethylformamide were 5 g of N,N-dimethylaminoethyl methacrylate, 7.9 g of dodecyl bromide and 0.6 g of dibutylhydroxytoluene as a polymerization inhibitor, and thereafter the solution was heated at 60° C. for 60 hours to obtain 11.0 g of a quaternized monomer (N,N-dimethyl-N-dodecylammonioethyl methacrylate bromide). Subsequently, 5 g of the resulting quaternized monomer and 5 g of sodium heparin were each dissolved in 50 ml of water, followed by blending to produce an ionically bonded composite, which was thereafter separated and collected. The sulfur content in this ionically bonded composite was found to be 4.5% as a result of elementary analysis. The ash content value was also found to be 0%.

Subsequently, prepared was a dimethylformamide solution so as to comprise 4% of the ionically bonded composite, 10% of polyurethane, 5% of N-vinylpyrrolidone, 1% of ethylene glycol dimethacrylate and 0.01% of azobisisobutyronitrile. Thereafter, the solution was heated with stirring at 60° C. for 48 hours in a nitrogen atmosphere to effect polymerization, thus obtaining an anticoagulant material. Next, the resulting anticoagulant material was purified. The ash content value thereof was found to be 0% as a result of elementary analysis. Thereafter, the anticoagulant material was formed into a 10% by weight dmethylformamide solution, and then this solution was coated on the inner wall of a polyurethane tube having an inner diameter of 10 mm and closed at its one end, followed by drying. Thus, a polymer layer (a layer of the anticoagulant material) was formed on the inner surface of the test tube.

Next, the inside of the above test tube was filled with a physiological saline, which was then maintained at 37° C. for 1 hour, and thereafter the physiological saline was removed. Subsequently, 1 ml of fresh rabbit blood was injected into the test tube, and thereafter the Lee-White test described in Clinical Examination Handbook (Kanahara Shuppan, 29th Revised Ed., 1983) was carried out to observe the state of the injected blood. As a result, no coagulation of the blood was seen even after lapse of 2 hours, and also no thrombus was seen at all on the inner wall of the test tube.

Thereafter, the blood in the test tube was removed and, after the test tube was thoroughly rinsed with a physiological saline, the Lee-White test was again carried out. As a result, no coagulation of blood and no thrombus on the inner wall of the test tube were seen at all.

Thereafter, the blood in the test tube was removed and, after the test tube was thoroughly rinsed with a physiological saline, the Lee-White test was again carried out, which was thereafter further repeated to carry out the Lee-White tests 15 times in total. As a result, no coagulation of blood and no thrombus on the inner wall of the test tube were seen at all. In a comparative example where only polyurethane was coated on the inner wall of the test tube, the blood coagulated in about 30 minutes on the first Lee-White test carried out.

It was clear from the above results that the anticoagulant material of this invention has superior anticoagulant properties.

Example 2

Dissolved in 80 ml of dimethylformamide were 5 g of N,N-dimethylaminoethyl methacrylate, 10.6 g of octadecyl bromide and 0.6 g of dibutylhydroxytoluene as a polymerization inhibitor, and thereafter the solution was heated at 60° C. for 60 hours to obtain 12.8 g of a quaternized monomer (N,N-dimethyl-N-octadecylammonioethyl methacrylate bromide). Subsequently, 5 g of the resulting quaternized monomer and 5 g of sodium heparin were each dissolved in 50 ml of water, followed by blending to produce an ionically bonded composite, which was thereafter separated and collected. The sulfur content in this ionically bonded composite was found to be 3.8% as a result of elementary analysis. The ash content value was also found to be 0%.

Subsequently, prepared was a dimethylformamide solution so as to comprise 4% of the ionically bonded composite, 10% of polyurethane, 4% of hydroxyethyl methacrylate, 1% methyl methacrylate, 1% of diethylene glycol dimethacrylate and 0.01% of lauroyl peroxide.

Using such a solution, polymerization and purification were carried out and the resulting anticoagulant material was formed into a dimethylformamide solution in the same manner as in Example 1, thus forming a polymer layer (a layer of the anticoagulant material) on the inner surface of the test tube. Subsequently, using this test tube, the Lee-White tests were carried out in the same manner as in Example 1. As a result, there were obtained entirely the same results as in Example 1.

Example 3

Dissolved in 80 ml of dimethylformamide were 5 g of N(N,N-dimethylaminopropyl)methacrylamide, 9.3 g of hexadecyl bromide and 0.6 g of dibutylhydroxytoluene as a polymerization inhibitor, and thereafter the solution was heated at 60° C. for 60 hours to obtain 11.4 g of a quaternized monomer (N,N-dimethyl-N-hexadecylammonioethyl methacrylate bromide). Subsequently, 5 g of the resulting quaternized monomer and 5 g of sodium heparin were each dissolved in 50 ml of water, followed by blending to produce an ionically bonded composite, which was thereafter separated and collected. The sulfur content in this ionically bonded composite was found to be 4.0% as a result of elementary analysis. The ash content value was also found to be 0%.

Subsequently, prepared was a dimethylformamide solution so as to comprise 3% of the ionically bonded composite, 11% of polyurethane, 5% of methacrylamide, 1% of methylenebismethacrylamide and 0.01% of azobisisobutyronitrile.

Using such a solution, polymerization and purification were carried out and the resulting anticoagulant material was formed into a dimethylformamide solution in the same manner as in Example 1, thus forming a polymer layer (a layer of the anticoagulant material) on the inner surface of the test tube. Subsequently, using this test tube, the Lee-White tests were carried out in the same manner as in Example 1. As a result, there were obtained entirely the same results as in Example 1.

Comparative Examples 1 to 3

Prepared were dimethylformamide solutions of anticoagulant materials for comparison, that were polymerized and purified under entirely the same composition except that the ionically bonded composite used in Examples 1 to 3 each was replaced by the quaternized monomer available before introduction of heparin which monomer was mixed in the same amount with that of said ionically bonded composite. A small amount of ethanol was added in the reaction mixture.

Using each of such solutions, polymer layers were formed on the inner surfaces of test tubes in the same manner as in Example 1. Subsequently, using these test tubes, the Lee-White tests were carried out in the same manner as in Example 1. As a result, the blood coagulated in about 30 to 40 minutes on each of the first Lee-White tests carried out.

Comparative Examples 4 to 6

Prepared were dimethylformamide solutions of anticoagulant materials, that were polymerized and purified under entirely the same composition except that the ionically bonded composite used in Examples 1 to 3 each was replaced by the same amount of an ionically bonded composite obtained from 5 g of benzalkonium chloride and 5 g of sodium heparin by the reaction in aqueous solution.

Using each of such solutions, polymer layers were formed on the inner surfaces of test tubes in the same manner as in Example 1. Subsequently, using these test tubes, the Lee-White tests were carried out in the same manner as in Example 1. As a result, on each of the fifth or sixth tests, thrombi were seen on the polymer layers formed on the inner walls of the test tubes, and, on the seventh or eighth tests, blood coagulation was seen in two hours in all cases. Also, hemolysis was seen in all cases after the first tests were carried out.

Comparative Examples 7 to 9

Using dimethylformamide solutions of the anticoagulant materials for comparison, prepared respectively in Comparative Examples 1 to 3, the solutions were coated in the same manner as in Example 1 on the inner walls of test tubes made of polyurethane, followed by drying to remove dimethylformamide. Thereafter an aqueous 5% sodium heparin solution was injected into each test tube, and then heating was carried out at 60° C. for 48 hours to effect introduction of heparin.

Using each of such test tubes, the Lee-White tests were carried out in the same manner as in Example 1. As a result, on each of the seventh or eighth tests, thrombi were seen on the polymer layers formed on the inner walls of the test tubes, and, on the tenth or eleventh tests, blood coagulation was seen in two hours in all cases.

Examples 4 to 6

Test tubes on their inner walls with the anticoagulant materials prepared in Examples 1 to 3 were filled with physiological salines, respectively, which were maintained at 37° C. for 1 hour, and thereafter the physiological salines were removed. Subsequently, 9 parts by volume of fresh human blood and 1 part by volume, based thereon, of an aqueous 3.8% sodium citrate solution were added to each test tube, and thereafter poor platelet plasma (PPP) obtained by centrifugal separation was poured into it, which was maintained at 37° C. After 30 minutes and after 1 hour, 0.1 ml each of PPP was collected and thromboplastin was added to measure coagulation time, whereupon the coagulation time was found to be 12 or 13 seconds, showing no significant difference from coagulation time of a control (about 12 seconds). This shows that heparin is remarkably restrained from flowing into the plasma.

Comparative Examples 10 to 12

Using test tubes coated on their inner walls with the anticoagulant materials prepared in Comparative Examples 7 to 9 followed by heparin introduction, the same tests as in Examples 4 to 6 were carried out to have found that the coagulation time was not less than 1 hour. This results from the flowing-out of heparin in large quantity into plasma.

Examples 7 to 9

Using the anticoagulant materials obtained respectively in Examples 1 to 3, prepared were 20% by weight dimethylformamide solutions of these. Next, stainless steel rods of 5 mm in diameter were sufficiently immersed in the solutions, and thereafter taken out to evaporate dimethylformamide under reduced pressure. In this manner, a layer comprising the anticoagulant material was formed on the periphery of each rod. Subsequently, the stainless steel rods were pulled out to obtain tubes of about 0.5 to 1 mm in thickness and 5 mm in inner diameter, each having a smooth inner wall.

The tubes thus obtained were cut into lengths of about 2.5 cm and were each inserted in an abdominal aorta of an adult dog, where observed were periods during which tubes were patent. As a result, tubes were patent even after lapse of 3 months. The tubes were also taken out to make observation on their inner walls, but thrombi were little observed.

Comparative Examples 13 to 15

Using the anticoagulant materials for comparison, prepared respectively in Comparative Examples 1 to 3, tubes each having the same shape and a smooth inner wall were obtained in the same manner as in Examples 7 to 9. Subsequently, the resulting tubes were immersed in an aqueous 5% sodium heparin solution to effect introduction of heparin at 60° C. over a period of 48 hours.

Such respective tubes thus obtained were cut into lengths of about 25 cm and were each inserted in an abdominal aorta of an adult dog, where observed were how tubes were patent. As a result, thrombi were generated inside the tubes in about 2 months in all cases, resulting in obturation of the tubes.

Examples 10 to 12

Using the anticoagulant materials obtained respectively in Examples 1 to 3, prepared were 20% by weight dimethylformamide solutions of these. Next, stainless steel rods of 5 mm in diameter were sufficiently immersed in the solutions, and thereafter taken out and immediately immersed in a large quantity of ethanol to effect solidification. Thereafter, dimethylformamide was removed and then the rods were taken out. In this manner, a layer comprising the anticoagulant material was formed on the periphery of each rod. Subsequently, the stainless steel rods were pulled out to obtain tubes of about 0.7 to 1.2 mm in thickness and 5 mm in inner diameter, each having uneveness on its inner and outer walls.

The resulting tubes were cut into lengths of about 2.5 cm and were each inserted in an abdominal aorta of an adult dog, where observed were how tubes were patent. As a result, tubes were patent even after lapse of 3 months in all cases. The tubes were also taken out to make observation on their inner walls, but thrombi were little observed.

As having described above in detail, the anticoagulant material of this invention can maintain very good anticoagulant properties (or antithrombotic properties) over a long period of time. This is because the heparin having anticoagulant properties is firmly bonded and held in the above material in a slightly water-soluble form by virtue of ionic bonding at many points, thus extremely suppressing its flowing into blood. Also, when the cross-linking agent is used, the Component (A) polymer and the Component (B) polymeric compound serving as a matrix is supposed to form the interpenetrating or entangling construction in the resulting anticoagulant material. Accordingly, when, for example, compared with a mere mixture of the above Component (A) with Component (B), the heparin can be held not only by the ionic bonding but also the physical network structure, so that the power to maintain anticoagulant properties can be further increased and also even the mechanical properties can be enhanced.

We claim:

1. An anti-thrombotic material comprising a heparin carrying polymer formed by
reacting (i) a basic monomer having a copolymerizable functional group and a functional group being capable of undergoing ionic bonding to a heparin salt; with (ii) a heparin salt, to form an ionically bonded composite with copolymerizable functional groups; and thereafter
homopolymerizing the copolymerizable functional group on the ionically bonded composite or copolymerizing the same group with at least one of a hydrophilic monomer rand a hydrophobic monomer and, optionally, a cross-linking agent to form the heparin carrying polymer; and wherein the ionic bonding in said ionically bonded composite is effected in substantially ion equivalent weight and the heparin salt is not released substantially at a physiological temperature.

2. The anti-thrombotic material according to claim 1, wherein the basic compound having a copolymerizable functional group is a compound having a vinyl group, an acryloyl group or a methacryloyl group as the copolymerizable functional group, and having a tertiary amino group, a quaternary ammonium group or a quaternary pyridinium group as a basic residual group, and capable of undergoing ionic bonding to the heparin salt to form a composite that is slightly soluble in water and soluble in an organic solvent.

3. The anti-thrombotic material according to claim 1, wherein said basic compound having a copolymerizable functional group is a compound represented by the following Formula (I):

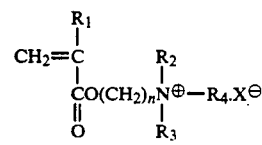

wherein $R_1$ represents a hydrogen, atom or a methyl group; $R_2$ and $R_3$ may be the same or different and each represent an alkyl group having 1 to 3 carbon atoms; $R_4$ represents an alkyl group having 6 to 22 carbon atoms; X represents a group of negative atoms; and n represents an integer of 1 to 6.

4. The anti-thrombotic material according to claim 3, wherein the group $R_4$ is an alkyl group having 8 to 18 carbon atoms and the group of negative atoms represented by X is halogen atoms.

5. The anti-thrombotic material according to claim 1, wherein the heparin salt is contained in said ionically bonded composite in an amount of from 0.5 to 12% by weight as the amount of the sulfur contained in the heparin salt.

6. The anti-thrombotic material according to claim 1, wherein the heparin salt is sodium heparin.

7. The anti-thrombotic material according to claim 1, wherein said polymerizing step comprises copolymerizing the functional groups with at least one of a hydrophilic monomer and a hydrophobic monomer that are copolymerizable with the ionically bonded composite and, optionally, a cross-linking agent.

8. The anti-thrombotic material according to claim 7, wherein the anticoagulant material further comprises a polymeric compound serving as a matrix to provide the anticoagulant material with an interpenetrating or entangling construction.

9. The anti-thrombotic material according to claim 8, wherein the polymeric compound serving as a matrix is at least one selected from the group consisting of polyvinyl chloride, polyvinyl acetate, polyacrylonitrile, polyepichlorohydrin, polyurethane, polyurethaneurea, acetyl cellulose, polyhydroxyethyl acrylate, polyhydroxymethacrylate and copolymers or mixtures thereof.

10. The anti-thrombotic material according to claim 7, wherein said hydrophilic monomer that is copolymerizable with the ionically bonded composite is used and is at least one selected from the group consisting of sodium acrylate, sodium methacrylate, acrylamide, methacrylamide, N-methyl acrylamide, acrylglycine amide, hydroxyethyl acrylate, hydroxyethyl methacrylate, methoxypolyethylene glycol acrylate, methoxypolyethylene glycol methacrylate, N-vinyl-pyrrolidone, N-vinyl-lactam, and diacetone acrylamide.

11. The anti-thrombotic material according to claim 7, wherein said hydrophobic monomer that is copolymerizable with the ionically bonded composite is used and is at least one selected from the group consisting of styrene, vinyl chloride, vinyl acetate, methyl acrylate, methyl methacrylate, acrylonitrile, methacrylonitrile, alkyl-substituted styrenes, vinyl isobutyl ether, vinyl propionate, and vinyl butyrate.

12. The anti-thrombotic material according to claim 7, wherein said cross-linking agent is used and is at least one selected from the group consisting of divinylbenzene, alkylenebisacrylamides, methacrylamides, alkylene glycol diacrylates or dimethacrylates, diethylene glycol diacrylate and dimethacrylate.

* * * * *